US006479257B1

(12) United States Patent
Miyauchi et al.

(10) Patent No.: US 6,479,257 B1
(45) Date of Patent: Nov. 12, 2002

(54) METHOD OF ACTIVATING PROTEIN AND AN APPARATUS THEREFOR

(75) Inventors: Akira Miyauchi, Choshi (JP); Makoto Ozawa, Choshi (JP); Masato Yoshida, Choshi (JP); Makoto Mizukami, Ibaraki-ken (JP)

(73) Assignee: Higeta Shoyu Co., Ltd., Tokyo (JP)

( * ) Notice: Subject to any disclaimer, the term of this patent is extended or adjusted under 35 U.S.C. 154(b) by 0 days.

(21) Appl. No.: 09/405,085

(22) Filed: Sep. 27, 1999

(30) Foreign Application Priority Data

Mar. 3, 1999 (JP) ............................................ 11-055715

(51) Int. Cl.$^7$ ............................. C12P 21/06; C12P 1/00
(52) U.S. Cl. ......................................... 435/69.1; 435/41
(58) Field of Search ................... 435/69.1, 41

(56) References Cited

U.S. PATENT DOCUMENTS

| | | | |
|---|---|---|---|
| 5,252,708 A | | 10/1993 | Abecassis et al. |
| 5,683,980 A | * | 11/1997 | Nilsson et al. .................. 514/3 |
| 5,719,021 A | | 2/1998 | Inouye |
| 5,861,150 A | * | 1/1999 | Halenbeck et al. ......... 424/85.1 |
| 5,874,247 A | | 2/1999 | Toyoshima et al. |
| 6,221,355 B1 | * | 4/2001 | Dowdy ..................... 424/192.1 |

FOREIGN PATENT DOCUMENTS

| | | |
|---|---|---|
| EP | 0 396 106 | 11/1990 |
| JP | 59-161321 | 9/1984 |
| WO | WO 96/03425 | 2/1996 |
| WO | WO 97/38123 | 10/1997 |

OTHER PUBLICATIONS

Sharp, R. J., "The Preservation of Genetically Unstable Microorganisms and the Cryopreservation of Fermentation Seed Cultures", Advances in Biotechnological Processes, Alan R. Liss, Inc., New York, vol. 3, pp. 81–109 (1984).*

A. Miyauchi, et al., Biosci. Biotechnol. Biochem., vol. 63, No. 11, pp. 1965 to 1969, "Structural Conversion from Non–Native to Native Form of Recombinant Human Epidermal Growth Factor by *Brevibacillus Choshinensis*", Nov. 1999.

J–Y. Chang, et al., The Journal of Biological Chemistry, vol. 270, No. 16, pp. 9207 to 9216, "The Disulfide Folding Pathway of Human Epidermal Growth Factor", 1995.

H. Tojo, et al., Journal of Biotechnology, vol. 33, No. 1, pp. 55 to 62, "Production of Human Protein Disulfide Isomerase by *Bacillus Brevis*", 1994.

Derwent Publications, AN 2000–026818, JP 11 285398, Oct. 19, 1999.

O. Shida, et al., International Journal of Systematic Bacteriology, vol. 46, No. 4, pp. 939–946, "Proposal For Two New Genera, Brevibacillus Gen. Nov. And Aneurinibacillus Gen. Nov.", Oct, 1996.

A. Miyauchi, et al., Journal of Industrial Microbiology and Biotechnology, vol. 21, pp. 208–214, "Pilot Scale Production of a Recombinant Human Epidermal Growth Factor, Secreted by *Bacillus Brevis*, Using Expanded Bed Adsorption", 1998.

* cited by examiner

Primary Examiner—Gary Benzion
Assistant Examiner—Teresa Strzelecka
(74) Attorney, Agent, or Firm—Oblon, Spivak, McClelland, Maier & Neustadt, P.C.

(57) ABSTRACT

The present invention relates to a method for activating protein wherein protein produced in a biologically inactive form (non-natural-form protein) is converted into a biologically active protein (natural-form protein) by bringing it into contact with cultured cells of an organism, and according to the present invention, the non-natural-form protein can be converted efficiently into the natural-form protein having activity, so the yield of the natural-form protein can be further raised by subjecting, e.g., culture of transformant to the activation treatment.

12 Claims, 4 Drawing Sheets

METHOD OF ACTIVATING PROTEIN AND AN APPARATUS THEREFOR

DETAILED DESCRIPTION OF THE INVENTION

1. Technical Field to which the Invention Belongs

The present invention relates to a method for converting protein produced in a biologically inactive form into natural-form protein (native-form protein) having activity when the protein is in a biologically inactive non-natural state (non-native-form) for the reason that its stereostructure is a higher-order structure biologically different from that of the natural protein having a normal biological activity, or for any other reasons.

The present invention relates to a method for converting protein which for some reasons, is rendered biologically inactive thus failing to have a biological activity which it would have in its normal stereostructure, into biologically active protein, as well as to an apparatus therefor. More specifically, the present invention relates to a method for activating protein, e.g., produced in transformant by means of genetic engineering and rendered biologically inactive due to formation of a stereostructure different from that of its natural protein.

2. Prior Art

Enzymes derived from organisms, peptides and proteins having a biological activity such as cytokine, came to be producible in a large amount by use of microorganisms, animal and plant cultured cells. However, it is known that heterologous proteins expressed in microorganisms as hosts often undergo denaturation in the host cells and occur in biologically inactive forms as precipitates. Further, even if produced and secreted extracellularly, the presence of peptides or proteins in biologically inactive forms are also known. One speculative reason is that although the proteins have the same primary structures as those of their natural types, their stereostructures are biologically not correctly constituted, thus failing to attain structures having biological activities.

Further, it is known that chemically synthesized polypeptides and biosynthesized proteins in cell extracts (cell-free system) often fail to have correct stereostructures, and these have, e.g., inactive structures with relatively less folding lacking in disulfide linkages.

JP-A 59-161321 discloses a method for restoring the activity of protein in a biologically inactive state failing to attain a correct stereostructure owing to incomplete disulfide linkages, wherein precipitated inactive protein is solubilized with a strong detergent, then the solubilized fluid is diluted or the strong detergent is replaced by a weak detergent thereby making the inactive protein active, and the biologically active protein is then recovered. However, this prior art method suffers from the problems that the volume of the protein solution is significantly increased and the activation is time-consuming. Further, because it is difficult to derive a general principle applicable in common to activation of a wide variety of proteins in said method, much endeavor as well as repeated trial and error are actually required for determining conditions for each individual protein of interest. No satisfactory method has been developed.

PROBLEMS TO BE SOLVED BY THE INVENTION

To raise the yield of a target protein produced by, e.g., recombinant DNA technology, it is conventional to take approaches to improving a gene, e.g., for modification of a signal peptide or to improving a method of culturing a transformant. Contrary to the prior art, the present application is drawn to an indirect method for raising the yield of target protein not by directly raising the yield thereof, but by converting inactive protein produced in a culture into an active type, and the object of the present invention is to provide a method for activating protein not having a biological activity for reason of failing to have an active stereostructure or for any other reasons, so that the protein can be converted into biologically active protein very easily and rapidly as compared with the previously proposed or practiced methods.

Further, the present invention provides a method for separating and fractionating protein produced in a biologically inactive form from a solution containing both protein produced in a biologically active form and the protein produced in a biologically inactive form, wherein the protein produced in a biologically inactive form resulting from, e.g., incorrect disulfide linkages is specifically aggregated, precipitated and recovered. As a matter of course, the inactive protein separated and fractionated in this manner can also be activated by the activation method described above.

MEANS FOR SOLVING THE PROBLEMS

Figure 1:
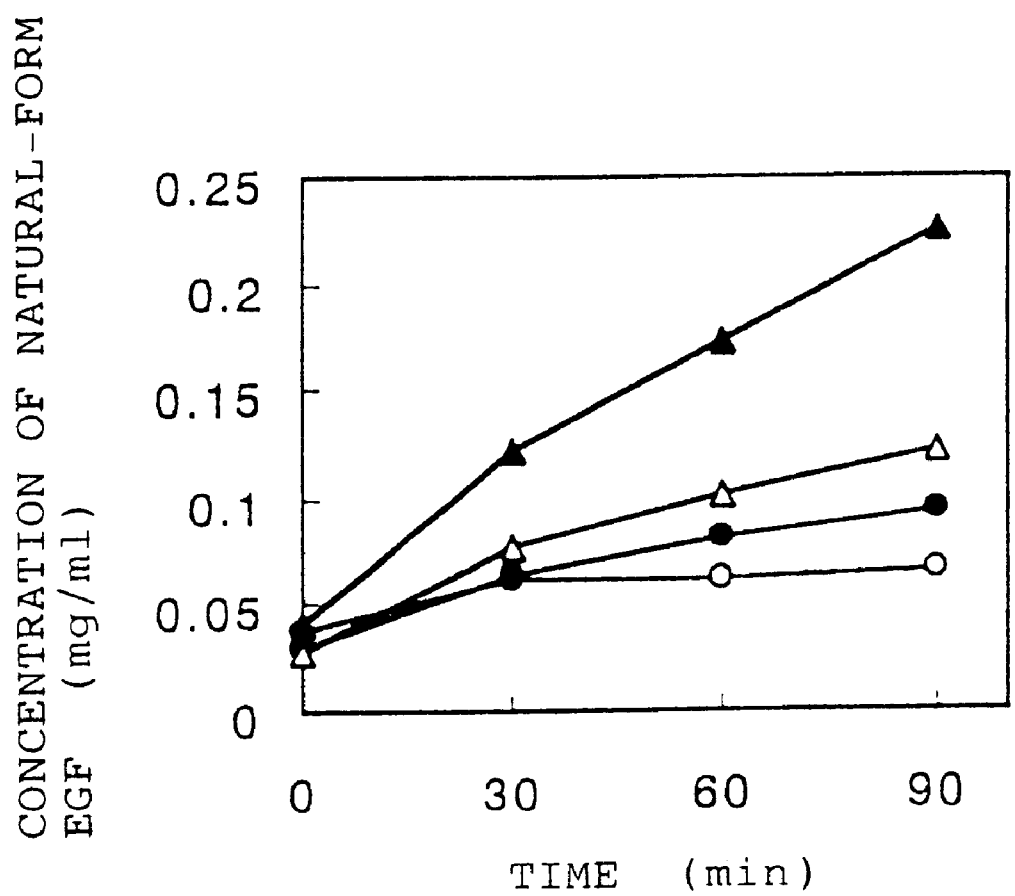
FIG. 1 is a graph showing the conversion of inactive EGF into active EGF (natural-form) by the cells of *Brevibacillus choshinensis*.
Figure 2:
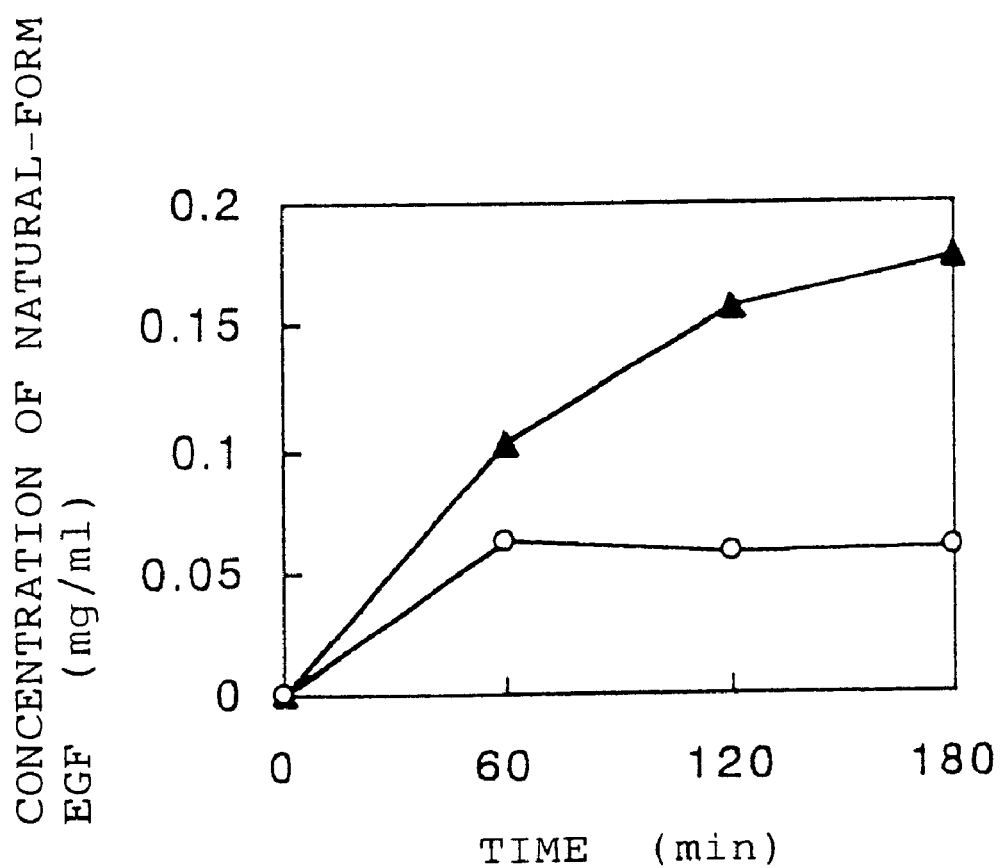
FIG. 2 is a graph showing the conversion of inactive EGF into active EGF (natural-form) by the cells of *Bacillus subtilis*.

The present invention was made to achieve the object described above, and as a result of eager study, the present inventors first found that when protein (multimeric EGF) not having a biological activity for reason of failing to achieve a normal stereostructure is incubated in a suspension of cultured cells of bacteria of the genus Brevibacillus, its stereostructure is normalized and its original biological activity is thereby restored, and the protein is thus converted into active EGF (native-form). As a result of additional examination, the present invention was thereby completed.

That is, the present invention relates to a method for activating protein wherein protein produced in a biologically inactive form is converted into biologically active protein by bringing it into contact with cultured cells of organism, and thus the present invention provides an extremely efficient and industrial method wherein every non-natural (non-native) protein, regardless of whether it is inactivated for reason of its biologically incorrect stereostructure or for any other reasons, can be activated and converted into its corresponding natural protein by the extremely easy operation of contacting the protein with cultured cells.

Hereinafter, the present invention is described in detail.

(1) The cultured cells of organisms used in the present invention may be human established cells derived from human renal cancer tissues, mouse myeloma cells, various hybridoma cells etc. The plant cells used in the present invention may be tobacco cells, rice cultured cells etc. The microbial cells used in the present invention may be those having prokaryotic cells, such as bacteria of the genus Escherichia, bacteria of the genus Bacillus, bacteria of Brevibacillus etc., or those having eukaryotic cells, such as yeasts of the genus Saccharomyces, yeasts of the genus Pichia, fungi of the genus Aspergillus etc.

The cultured cells described above can be used as necessary, and particularly for industrial purposes, the cells are preferably those capable of large-scale culture, more preferably cells of fungi, yeasts and bacteria which are cultured preferably under aerobic conditions. In particular, the genera Escherichia, Bacillus, Brevibacillus and yeasts whose industrial and large-scale production has been established can be used more preferably. Among bacteria of the genus Brevibacillus, *Brevibaccillus choshinensis* HPD31 does not produce a proteolytic enzyme in a culture (This strain was deposited as *Bacillus brevis* H102, FERM BP-1087 on Jun. 24, 1986 and renamed as *Brevibacillus choshinensis* HPD31, FERM BP-1087 and the deposition runs. However, many years have passed since the date of the deposition, and therefore this strain was newly deposited on Aug. 31, 1999 under the Budapest Treaty in the same depository and alloted No. FERM BP-6863. Depository: International Patent Organism Depositary, National Institute of Advanced Industrial Science and Technology, AIST Tsukuba Central 6,1-1, Higashi 1-chome, Tsukuba-shi, Ibaraki-ken, 305-8566, Japan. Further, this strain is the same strain as *Bacillus brevis* HPD31. Its position in classification was altered in International Journal of Systematic Bacteriology, Vol. 46, pp. 939–946 (1996)), and by use of this bacterium, protein having no biological activity is converted into activated protein having a normal stereostructure and this protein is accumulated without undergoing decomposition during reaction, thus permitting the process of the present invention to be carried out very efficiently. Further, because no proteolytic enzyme occurs in the medium, the culture or the cells collected by centrifugation can be used advantageously as such without worrying about decomposition of the activated protein.

(2) The culture method is varied depending on the genus and species of cells used, but any medium may be used insofar as the cells can be cultured and proliferated therein in a conventional culture method. For example, it is possible to use cultured cells harvested after proliferation by a culture method such as a liquid shake culture method, an agar plate culture method, a solid culture method, an aeration stirring culture method etc. The cells thus cultured may be used in the form of culture itself containing the cells, or the cells may be used as such after collection by centrifugation or by filtration of the culture through an MF membrane (microfiltration membrane), or may be used after washing with various buffers. The collected cells may be lyophilized and suspended in a buffer before use, or may be suspended in a buffer for freezing storage, frozen for storage, and thawed before use. As described above, the cultured cells used in the present invention may be used in at least one form selected from the group consisting of culture, cells harvested by centrifugation etc., lyophilized cells, cells in the form of suspension of lyophilized cells in a suitable buffer, any suspended cells after cultured cells were lyophilized and thawed; but in any cases, these should be used as undisrupted (undestroyed) cells.

(3) The protein to be activated includes various polypeptides chemically synthesized using a peptide synthesizer, various proteins synthesized in an in vitro protein synthesis system using a rabbit reticulocyte extract, various proteins produced by recombinant DNA technology, and materials containing such protein(s). The protein produced by recombinant DNA technology include (1) protein itself, (2) the whole culture (culture of transformant used) containing protein produced, (3) biologically inactive protein separated and fractionated from the culture, and (4) material containing at least one member selected from the group consisting of (1) to (3).

Examples of such proteins include enzymes, hormones, cytokines, lymphokines, receptors etc., and further specific examples include urokinase, insulin, tissue plasminogen activator, erythropoietin, interleukin receptors and various growth factors, proteins analogous to growth factors such as epidermal growth factor, insulin-like growth factor etc., immunoglobulins, single-stranded antibodies etc. In particular, some proteins produced by recombinant DNA technology using *E. coli* as the host are produced in a large amount, but there are a large number of known cases where the proteins fail to their correct stereostructure, and thus occur as insoluble granules in the cells.

Some recombinant proteins secreted into the outside of the cells are insolubilized in the outside of the cells, or fail to attain their correct structures, thus being aggregated and produced in a multimeric state, depending on their type. Usually, such proteins have incorrectly bridged disulfide linkages to form incorrect linkages. Therefore, these proteins, though having the correct primary structure, have different stereostructures different from those of the active types, thus failing to have their biological activities. The present invention relates to a method of converting such protein into a biologically active protein by bringing it into contact with cultured cells in order to reconstitute disulfide linkages into correct ones, that is, a method of activating the protein produced in a biologically inactive state.

(4) To carry out the present invention, the protein to be activated is brought into contact with cultured cells. Bringing the protein produced in a biologically inactive state into contact with cultured cells of organism involves bringing it into contact at least one member selected from the group consisting of cultured cells themselves, culture containing cultured cells, washed cultured-cells, immobilized cultured-cells, lyophilized cultured-cells, and suspension of at least one member selected from the group consisting of them. Although the mechanism of the activation according to the present invention has not been elucidated, one speculative reason is that disulfide linkages are normalized.

In the method of activating protein according to the present invention, the best embodiments can be selected for the contact manner and the amount of cultured cells to be contacted with protein produced in a biologically inactive state. For example, if microorganisms having prokaryotic cells are used as the cultured cells, the microbial cells are suspended in a suitable buffer, e. g., Tris-HCl buffer, and the suspension is added in excess to protein produced in an inactive state, mixed well, incubated for 1 to 2 hours preferably at 15 to 60° C., more preferably at 25 to 45° C., whereby the protein produced in a biologically inactive state is activated.

For the contact, the cultured cells are enveloped with or immobilized on in an MF membrane (micro filtration membrane) etc., and a protein solution prepared by dissolving in buffer etc. is brought into contact with the cells by passing it through the membrane, or alternatively the cells are adsorbed on carrier such as hydrophobic porous resin HP-20 (Mitsubishi Chemicals Co.) to prepare an immobilization column, and the protein solution may be brought into contact with the cells by feeding it to the immobilization column.

The activation apparatus according to the present invention is to realize these steps specifically, and this apparatus includes cultured cells immobilized on an MF membrane or insoluble carrier, and a solution feeder such as pump by which a protein produced in a biologically inactive state is fed to in the form of solution and brought into contact with the immobilized cells, thereby activating the protein. In the apparatus, the cultured cells may be immobilized by conventional techniques of immobilization onto carriers for enzymes, various proteins and microorganisms, besides the means described above. That is, inorganic or organic, natural or synthetic, high-molecular or low-molecular, biological or non-biological various carriers may be used, and conventionally known immobilization techniques such as covalent bonding method, ionic bonding method, physical adsorption method etc. are utilizable as necessary.

As the carrier, are suitably usable polysaccharide (derivative) such as agarose, cellulose, dextran, Sepharose, Sephadex etc., synthetic high molecular material such as polyacrylamide gel, polystyrene etc., and inorganic or ceramic material such as glass (e.g., porous glass), ceramic (e.g., porous ceramic), activated carbon, silica gel, alumina, clay minerals etc. Immobilization may be carried out by bringing the cultured cells into contact with the carrier, or by bringing the cultured cells into contact with the carrier after the carrier is reacted with cyan bromide or cyanoboron hydride. Or the cultured cells maybe more strongly immobilized on the carrier after the carrier is treated with a cross-linking agent or a condensing agent.

The effect of the present invention can be improved more effectively by adding 0.1 to 50 mM compound having sulfhydryl group(s), such as reduced glutathione and cysteine, when the cultured cells are brought into contact with the protein which was produced in a biologically inactive form due to erroneous disulfide linkages.

Further, in the case of a mixture of natural-form protein and non-natural-form protein from which the protein to be activated is not isolated, the present invention provides a method for separating and fractionating the protein produced in a biologically inactive form, wherein a solution containing protein produced in a biologically active form and protein produced in an inactive form is adjusted to a pH value less than the isoelectric point of the biologically active form, whereby the protein produced in a biologically inactive form is specifically aggregated, precipitated and recovered. According to this method, the target active protein can be purified, and the recovered inactive protein can also be used as the protein to be activated.

In one example of the fractionation and separation method of the present invention, a solution containing recombinant epidermal growth factor produced in a biologically inactive form due to its erroneous disulfide linkages is adjusted to pH 3 whereby the recombinant epidermal growth factor as the protein produced in a biologically inactive form is specifically aggregated, precipitated and recovered.

Hereinafter, the present invention is described in more detail by reference to the Examples, which however are shown for illustrative purposes only and not intended to limit the present invention.

EXAMPLE 1

Preparation of Cultured Cells (1) Preparation of E. coli cells

Escherichia coli JM109 (Takara Shuzo Co., Ltd.) was cultured at 30° C. for 24 hours with shaking in a liquid medium containing 4 g polypeptone, 0.5 g yeast extract, 2 g glucose and 100 ml water (pH 7.0) and harvested by centrifugation, and the cells thus obtained were suspended in 100 ml of an aqueous 4% polypeptone solution.

(2) Preparation of Bacillus subtilis cells Bacillus subtilis IFO13719 was cultured at 30° C. for 24 hours with shaking in a liquid medium containing 4 g polypeptone, 0.5 g yeast extract, 2 g glucose and 100 ml water (pH 7.0) and harvested by centrifugation, and the cells thus obtained were suspended in 100 ml of an aqueous 4% polypeptone solution.

(3) Preparation of Brevibacillus choshinensis cells

Brevibacillus choshinensis HPD31 (FERM BP-1087) was cultured at 30° C. for 24 hours with shaking in a liquid medium containing 4 g polypeptone, 0.5 g yeast extract, 2 g glucose and 100 ml water (pH 7.0) and harvested by centrifugation, and the cells thus obtained were suspended in 100 ml of an aqueous 4% polypeptone solution.

(4) Preparation of yeast cells

Saccharomyces cerevisiae IFO10217 was cultured at 30° C. for 24 hours with shaking in a liquid medium containing 1 g peptone, 0.5 g yeast extract, 4 g glucose, 0.5 g $KH_2PO_4$, 0.2 g $MgSO_4.7H_2O$, and 100 ml water (pH 7.0) and harvested by centrifugation, and the cells thus obtained were suspended in 100 ml of an aqueous 1% peptone solution.

EXAMPLE 2

Method of Separating and Fractionating Protein Produced in an Inactive Form (1) Preparation of human recombinant epidermal growth factor (h-rEGF) produced in an inactive form.

Brevibacillus choshinensis HPD31 carrying plasmid pHT110EGF containing a gene for human recombinant epidermal growth factor, prepared by miyauchi et al. (Journal of Industrial Microbiology and Biotechnology, Vol. 21, pages 208–214 (1998)), was cultured in a liquid medium for 65 hours under the conditions described in the same literature, and the supernatant was recovered by centrifugation. It was adjusted to pH 3.0 with 6 M hydrochloric acid, and the human recombinant epidermal growth factor produced in an inactive form was specifically precipitated, and the resulting precipitate was recovered by centrifugation. The precipitate was dissolved in 0.1 M Tris-HCl (pH 7.0) and adjusted again to pH 3.0 with 6 M hydrochloric acid, and the precipitate was recovered by centrifugation. Further, the precipitate was suspended in distilled water, adjusted to pH 7.0 with aqueous sodium hydroxide and lyophilized to prepare inactive human recombinant epidermal growth factor (h-rEGF). This inactivated human recombinant epidermal growth factor (h-rEGF) is multimeric EGF (according to SDS-PAGE/Western Blotting analysis of the culture supernatant producing EGF), and it is non-natural-form (non-native-form) EGF whose inactivation is presumably due to intermolecular formation of S-S linkages between cysteine residues of neighboring EGF molecules.

EXAMPLE 3

Activation of Inactivated Proteins (1) Activation of inactive human recombinant epidermal growth factor (h-rEGF) by the cultured cells of Brevibacillus choshinensis.

The inactive h-rEGF obtained in Example 2-(1) was dissolved in distilled water to give a solution (dried matter 36 mg/ml). To 20 $\mu$l of the solution, were added (a) 20 $\mu$l of 1 M Tris-HCl buffer (pH 8.0), (b) 4 $\mu$l of 100 mM reduced glutathione, (c) 5 $\mu$l, 20 $\mu$l or 50 $\mu$l of a suspension prepared by diluting the suspension of Brevibacillus choshinensis obtained in Example 1-(3) with an aqueous 4% polypeptone solution so that the diluted suspension could show O.D. 10 at 660 nm, and (d) distilled water to give a mixed solution of 200 $\mu$l (total volume). The mixed solution was incubated at 30° C., and the conversion of the inactive multimeric EGF into active natural-form EGF was examined with time. The conversion of the multimeric EGF into natural-form EGF was quantified by HPLC. The conditions for HPLC analysis was conducted using Licrospher 100, RP-18 column (4×125 mm) (Merck Co.), and the protein was eluted by a gradient of from 25% to 34% acetonitrile containing 0.1% trifluoroacetic acid. The flow rate was 1.0 ml/min and the protein was detected at 280 nm. The increase of the area in a peak appearing at the retention time of standard HEGF was regarded as the amount of natural-form EGF converted. The conversion of the multimeric EGF into natural-form EGF is shown in the relationship between time (min, abscissa) and the amount of natural-form EGF produced (mg/ml, ordinate) in FIG. 1. The results of addition of 50 μl (▲), 20 μl (Δ) and 5 μl (●) of the *Brevibacillus choshinensis* cell suspension and the control (○) are shown. The control was prepared in the same manner as in the preparation of the mixed solution, provided that 50 μl of an aqueous 4% polypeptone solution was used in place of (c). When the *Brevibacillus choshinensis* cell suspension was added, the appearance of the natural-form EGF was promoted, and this conversion was increased as the density of the *Brevibacillus choshinensis* cells was increased. No addition of the suspension means the use of the polypeptone solution without containing the cells. This is also applied in the following (2) to (4).

(2) Activation of inactive human recombinant epidermal growth factor (h-rEGF) by the cultured cells of by *Bacillus subtilis*.

The inactive h-rEGF obtained in Example 2-(1) was dissolved in distilled water to give a solution (dried matter 36 mg/ml). To 20 μl of the solution, were added (a) 20 μl of 1 M Tris-HCl buffer (pH 8.0), (b) 4 μl of 100 mM reduced glutathione, (c) 50 μl of a suspension prepared by diluting the suspension of *Bacillus subtilis* obtained in Example 1-(2) with an aqueous 4% polyopeptone solution so that the diluted suspension could show O.D. 10 at 660 nm, and (d) distilled water to give a mixed solution of 200 μl (total volume). The mixed solution was incubated at 30° C., and the conversion of the inactive EGF into active natural-form EGF was examined with time. The conversion of the multimeric EGF into natural-form EGF was quantified by the same manner as in Example 3-(1). The conversion of the multimeric EGF into natural-form EGF is shown in the relationship between time (min, abscissa) and the amount of natural-form EGF produced (mg/ml, ordinate). The results of addition (▲) of the *Bacillus subtilis* cell suspension and the control (○) are shown. The control was prepared in the same manner as in the preparation of the mixed solution, provided that 50 μl of an aqueous 4% polypeptone solution was used in place of (c). When the *Bacillus subtilis* cell suspension was added, the appearance of natural-form EGF was promoted.

(3) Activation of inactive human recombinant epidermal growth factor (h-rEGF) by the cultured cells of *E. coli*.

Figure 3:
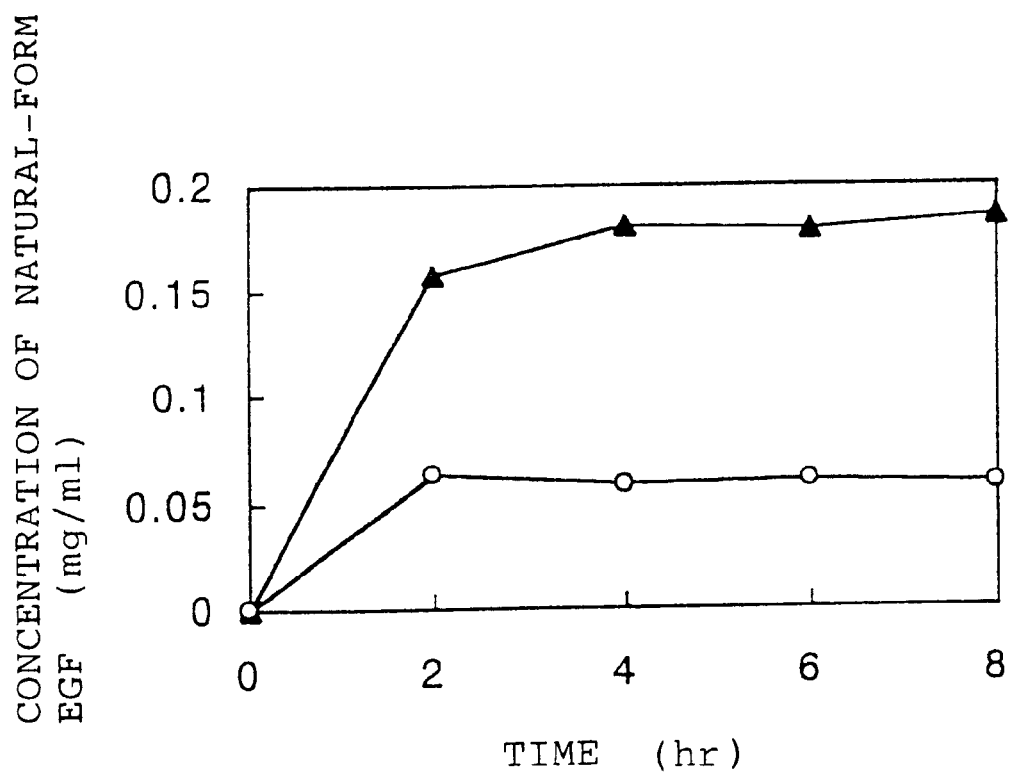
FIG. 3 is a graph showing the conversion of inactive EGF into active EGF (natural-form) in a reactor having the cells of *E. coli* immobilized therein.

A tangential flow-type filter Minitan II (Millipore Co.) equipped with a MF membrane (Durapore (trade name), Millipore Co. ) with pores, of which the diameters are 0.45 pm, was used as an immobilized cell reactor. The inactive h-rEGF obtained in Example 2-(1) was dissolved in distilled water to give a solution (dried matter 36 mg/ml). To 100 ml of the solution, were added (a) 100 ml of 1 M Tris-HCl buffer (pH 8.0), (b) 50 ml of a suspension prepared by diluting the suspension of *E. coli* obtained in Example 1-(1) with an aqueous 4% polypeptone solution so that the diluted suspension could shown O.D. 10 at 660 nm, (c) 20 ml of 100 mM reduced glutathione, and (d) 730 ml of distilled water to give a mixed solution of 1000 ml (total volume). Into the immobilized cell reactor installed in a thermostatic chamber set at 30° C., was fed the mixed solution at a flow rate of 10 ml/min from a server tank containing the mixed solution of 1000 ml by using a pump. The flow rate of the filtrate passed through the MF membrane was regulated to attain 1 ml/min by controlling the pressure at the outlet valve of the immobilized cell reactor; the filtrate contains the activated h-rEGF. A polypeptone-containing solution, which was prepared in the same manner as in the preparation of the mixed solution provided that 50 ml of an aqueous 4% polypeptone solution was used in place of (b), was fed to the server tank at the same flow rate as that of the filtrate (i.e., 1 ml/min to prevent the decrease of the volume of the solution in the immobilized cell reactor. The filtrate was recovered with time, and the conversion of the multimeric EGF into natural-form EGF was quantified in the same manner as in Example 3-(1). The change with time of conversion of the multimeric EGF into natural-form EGF is shown in the relationship between time (min, abscissa) and the amount of natural-form EGF produced (mg/ml, ordinate) in FIG. 3. In the case (▲) where the *E. coli* cell suspension was added at the start of the reaction, the conversion into natural-form EGF was promoted as compared with the case of the control (○), and further, the natural-form EGF was successively recovered for a long period of time. The control was prepared in the same manner as in the preparation of the mixed solution, provided that 50 ml of an aqueous 4% polypeptone solution was used in place of (b).

(4) Activation of inactive human recombinant epidermal growth factor (h-rEGF) by the cultured cells of yeast.

Figure 4:
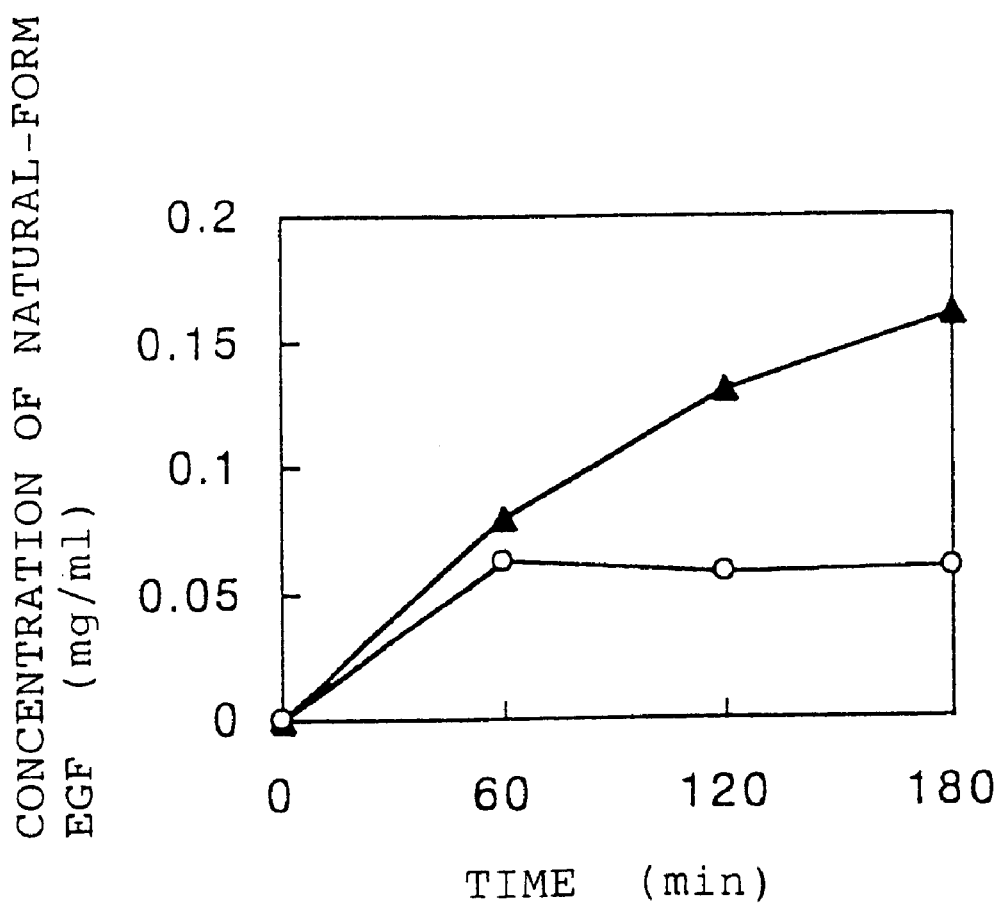
FIG. 4 is a graph showing the conversion of inactive EGF into active EGF (natural-form) by the cells of yeast.

The inactive h-rEGF obtained in Example 2-(1) was dissolved in distilled water to give a solution (dried matter 36 mg/ml). To 20 μl of the solution, were added (a) 20 μl of 1 M Tris-HCl (pH 8.0), (b) 4 μl of 100 mM reduced glutathione, (c) 50 μl of a suspension prepared by diluting the suspension of *S. cerevisiae* obtained in Example 1-(4) with an aqueous 1% polypeptone solution so that the diluted suspension could show O.D. 10 at 660 nm, and (d) distilled water to give a mixed solution of 200 μl (total volume). The mixed solution was incubated at 30° C., and the conversion of the inactive EGF into active natural form EGF was examined with time. The amount of natural-form EGF converted from the inactive EGF was examined in the method shown in Example 3-(1). The change with time of conversion from the multimeric EGF into natural-form EGF is shown in the relationship between time (min, abscissa) and the amount of natural-form EGF produced (mg/ml, ordinate) in FIG. 4. The results of addition (▲) of the yeast cell suspension and the control (○) are shown. The control was prepared in the same manner as in the preparation of the mixed solution, provided that 50 μl of an aqueous 1% polypeptone solution was used in place of (c). When the yeast cell suspension was added, the appearance of natural-form EGF was promoted.

Effects of the Invention

According to the present invention, inactive protein can be converted into active protein in the very easy treatment of bringing the protein into contact with cultured cells. Therefore, according to the activation method of the present invention, protein (often containing inactive protein, thus reducing the yield of active protein and further leading in some cases to no recovery) produced by chemical synthesis, biosynthesis, or recombinant DNA technology etc. can be activated, e.g., by incubating the produced culture containing inactive protein with culture cells, and as a result, the yield of natural-form protein having activity can be raised.

What is claimed is:

1. A method of converting a biologically-inactive form of a protein having disulfide linking produced by recombinant DNA technology to a biologically-active form of the protein, wherein the inactivity is due to erroneous intramolecular and/or intermolecular disulfide linking in the protein, comprising:

contacting the biologically-inactive form of the protein with live cultured cells of at least one member selected from the group consisting of bacterium and yeast in an aqueous solution, wherein the live cultured cells correct the erroneous disulfide linking in the protein.

2. The method according to claim 1, wherein the live cultured cells are provided by at least one member selected from the group consisting of:

(1) a culture containing cultured cells, (2) cultured cells isolated from a culture, (3) cultured cells thawed from lyophilized cultured cells, (4) resuspension of lyophilized cultured cells, and (5) immobilized cultured cells.

3. The method according to claim 2, wherein the live cultured cells are provided by (1).

4. The method according to claim 2, wherein the live cultured cells are provided by (2).

5. The method according to claim 2, wherein the live cultured cells are provided by (3).

6. The method according to claim 2, wherein the live cultured cells are provided by (4).

7. The method according to claim 2, wherein the live cultured cells are provided by (5).

8. The method according to claim 2, wherein the immobilized cultured cells are one member selected from the group consisting of (1) free cultured cells enveloped with a microfiltration membrane, (2) cultured cells immobilized on a microfiltration membrane or an insoluble carrier, and (3) cultured cells confined into a microfiltration membrane or an insoluble carrier.

9. The method according to claim 1, wherein the protein is selected from the group consisting of enzymes, hormones, cytokines, lymphokines, and receptors.

10. The method according to claim 9, wherein the cytokine is a growth factor.

11. The method according to claim 10, wherein the growth factor is epidermal growth factor (EGF).

12. The method according to claim 1, wherein the biologically-inactive form of the protein is one recovered by a method which comprises adjusting a pH value of a solution containing a biologically-active form of the same protein as well as the biologically-inactive form of the protein to a pH value which is less than the isoelectric point of the biologically-active form of the protein, thereby aggregating, precipitating and recovering the biologically-inactive form of the protein.

* * * * *